United States Patent [19]

Jones et al.

[11] 4,160,971
[45] Jul. 10, 1979

[54] TRANSPONDERS

[75] Inventors: Barry E. Jones; John A. Smith, both of Altrincham, England

[73] Assignee: National Research Development Corporation, London, England

[21] Appl. No.: 681,743

[22] Filed: Apr. 29, 1976

[30] Foreign Application Priority Data

May 2, 1975 [GB] United Kingdom ............... 18471/75

[51] Int. Cl.² .......................... H04Q 9/00; G01S 9/56
[52] U.S. Cl. ........................ 340/152 T; 343/6.5 SS; 340/505
[58] Field of Search .................. 340/280, 258 C, 224, 340/152 T; 343/6.5 SS, 6.8 R; 325/8; 317/134

[56] References Cited

U.S. PATENT DOCUMENTS

| | | | |
|---|---|---|---|
| 3,036,295 | 5/1962 | Kleist | 343/6.5 SS |
| 3,137,847 | 6/1964 | Kleist | 343/6.5 SS |
| 3,182,314 | 5/1965 | Kleist | 343/6.5 SS |
| 3,182,315 | 5/1965 | Sweeney | 343/6.5 SS |
| 3,218,638 | 11/1965 | Honig | 343/6.8 R |
| 3,299,424 | 1/1967 | Vinding | 343/6.8 R |
| 3,363,246 | 1/1968 | Gareis | 343/6.5 SS |
| 3,467,962 | 9/1969 | La Plume | 343/6.5 SS |
| 3,518,546 | 6/1970 | Augenblick | 325/8 |
| 3,522,602 | 8/1970 | Ver Planck | 343/6.8 R |
| 3,737,911 | 6/1973 | Sakaguri | 343/6.5 SS |
| 3,739,279 | 6/1973 | Hollis | 340/224 |

Primary Examiner—Harold I. Pitts
Attorney, Agent, or Firm—Cushman, Darby & Cushman

[57] ABSTRACT

A passive transponder, particularly for dental or medical applications, is described in which signals received by one or more receive resonant circuits are changed in frequency either up or down by a non-linear device coupled to one or more transmit resonant circuits. Each transmit resonant circuit includes a transducer whose impedance depends on a quantity whose value is to be transmitted and thus the frequency of signals received from the transponder depends on the value of the quantity.

33 Claims, 21 Drawing Figures

TRANSPONDERS

The present invention relates to transmitters without local power supplies which are remotely powered by transmissions received. Such transmitters are particularly, but not exclusively, useful in some telemetry applications where it is undesirable or not possible to provide a battery or other local power supply.

Radiotelemetry has long been applied to physiological monitoring using transmitters attached outside the body. The ready availability of transistors stimulated the development of a wide variety of telemetry systems and during the past two decades increasingly complex, low power consuming microelectronic circuits have been implanted within the body. Frequencies used covered the range from about 100 kHz to 500 MHz. Quantities of interest range from biopotentials, temperature, pressure, strain, pH and fluoride concentrations to movement and contact. A key component in a biotelemetry transducer system is the power source, normally an electrochemical battery. It is a large component (often determining the size of the transmitter), the one most liable to fail and restricts the period of unattended monitoring. To conserve the battery, complex controlled "on-off" switching has been employed.

An object of the invention is to provide a technique for telemetry using a passive sensing circuit (that is, a circuit which does not require its own battery). The technique is being applied in dentistry to measure pressure on dental plates but it is expected to find application in other biomedical and non-medical field particularly the telemetry of rotating parts.

Various passive sensing circuits have been used employing the "grid-dip" loading technique and methods of inducing currents into the sensing circuits. These approaches are either restricted to short range usage, require high induced voltage or cannot easily be used in multichannel applications.

According to a first aspect of the present invention there is provided transponder apparatus including receive and transmit resonant circuits resonant at first and second frequencies, respectively, and a non-linear device, having a pair of terminals between which a non-linear impedance appears when operating conditions for the device vary, the transmit resonant circuit being connected across, or in series with, the said terminals, and the receive resonant circuit being connected to so vary the said operating conditions, when signals of at least a predetemined strength are induced therein, that the non-linear impedance of the device varies cyclically.

The non-linear device may for example include a tunnel diode, a varactor diode, a step-recovery diode, an ultrasonic device or an optical device. A semiconductor junction diode has also been used.

According to a second aspect of the present invention there is provided transponder apparatus including receive and transmit resonant circuits resonant at first and second frequencies, respectively, and a negative resistance device, having a pair of terminals between which positive and negative resistances appear when operating conditions for the device vary, the transmit resonant circuit being connected across, or in series with, the said terminals, and the receive resonant circuit being connected to so vary the said operating conditions, when signals of at least a predetermined strength are induced therein, that the resistance of the device cyclically varies between positive and negative resistance.

The transmit resonant circuit may include a transducer which varies the second resonant frequency in accordance with a quantity measured (for example pressure, temperature, strain or pH). Such a transducer may employ inductive or capacitive variations, or a combination of these variations, and piezoelectric, microwave or optical transducers may for example be used. Signals are induced in the receive resonant circuit by a transmitter and these signals switch the negative resistance device cyclically through its negative resistance region and in so doing provide harmonics some of which have the resonant frequency of the transmit circuit. Signals are induced in a receiver by the selected harmonics in the transmit resonant circuit.

The signal from the negative resistance device "rings" the transmit resonant circuit and since the signal transmitted by the transponder is higher in frequency than that received, the transponder acts as a frequency "up-converter".

An important advantage of the invention is therefore that a transponder is provided which requires no internal power supply and which may generate a signal representative of a quantity to be measured. The transponder may take many shapes. For example it may be in small tablet form or in a longitudinal pill shaped form. The aerials might take the form of long thin coils or dipoles associated with the long thin tubes that can be inserted during cardiac monitoring. In general, range of operation can be traded for smaller passive transponder size. Small encapsulated transponders and transducers are expected to be used for long term monitoring of quantities inside the body (besides the dental application, use in the gut, bladder and brain is envisaged).

The negative resistance element may include a signal tunnel diode connected in parallel with the two resonant circuits. A doubling of data rate may usually be achieved if the negative resistance element includes two tunnel diodes connected back to back in parallel with the resonant circuits.

Apparatus according to the invention may also include a transmitter for transmitting signals at the first frequency.

The apparatus may also include a receiver having a receiving circuit broadly tuned to the frequency range in which second frequency occurs, and a frequency indicating circuit for providing a signal indicative of the second frequency.

Where two or more quantities are to be measured one or more further transmit resonant circuits may be connected across the said pair of terminals of the negative resistance device, for example the further resonant circuit or circuits may be connected across the tunnel diode or across the combination of two back to back tunnel diodes. Each further resonant circuit is resonant at a different frequency from all other such circuits of the apparatus and contains a transducer whose impedance varies in accordance with a quantity to be measured.

In a somewhat different form of the invention, the transmitter transmits both at a fixed frequency and at a sweep frequency which varies cyclically over a predetermined frequency range. The transponder then has an additional receive resonant circuit, one receive resonant circuit being resonant at the fixed frequency and the other being resonant at substantially the centre of the swept frequency range. A single transmit resonant circuit is provided which is resonant in the range of the difference between the fixed and sweep frequencies but at a frequency determined by a transducer. The aerial circuit of the receiver is tuned to the difference frequency range and a frequency-indicating circuit is provided for giving an indication of the instantaneous difference frequency. Here the transponder acts as a frequency "down converter" since the signal it transmits is lower in frequency than the signal it receives.

The frequency-indicating circuit may advantageously include first and second phase-sensitive detectors coupled to receive the output of the receiver aerial circuit and first and second reference signals, respectively. The first reference signal is in quadrature with the second reference signal but both are at the difference frequency. Means are provided for squaring and summing the output signals of the phase sensitive detectors to provide a high signal to noise ratio output dependent on the resonant frequency of the transmit resonant circuit.

The transmitter may be constructed to transmit an amplitude modulated signal (or the product of two signals) containing, a swept difference frequency component instead of two frequencies when only one receive resonant circuit is required in the transponder.

Each resonant circuit mentioned above may be either series or parallel resonant and although transmission and reception is usually by electromagnetic radiation, for example at radio frequencies by near field inductive links or far field microwave links, one or more of the resonant circuits may include a piezoelectric crystal so that either transmission or reception (or both) is by ultrasonic sound waves. The use of ultrasonic waves under water considerably increases the range of the system. A useful temperature transducer includes a piezo-electric crystal having a resonance which varies with temperature. When piezoelectric crystals are used in the transponder, impedance matching transformers may be used. Furthermore transmission to and from the transponder may be by optical link. Combinations of different links may prove useful.

In this specification the term "negative resistance device" means a device having two terminals between which under certain conditions an increase in voltage is accompanied by a decrease in current.

The first and second resonant circuits may have components common to both circuits, for example portions of inductors, either permanently connected in both circuits or connected by switching at appropriate times. Thus references to these circuits in this specification and the claims attached hereto include such circuits when constructed with one or more common components. In addition the transmitter and receiver mentioned for transmission to, and reception from the transponder, may include common components such as a single aerial coil, permanently connected or connected as appropriate during transmission and reception by switching circuits. Again, references to the transmitter and receiver, or components thereof, in this specification and the claims attached hereto, include such items when constructed with one or more common components.

BRIEF DESCRIPTION OF THE DRAWINGS

Certain embodiments of the invention will now be described by way of example, with reference to the accompanying drawings, in which.

DETAILED DESCRIPTION OF THE DRAWINGS

Figure 1:
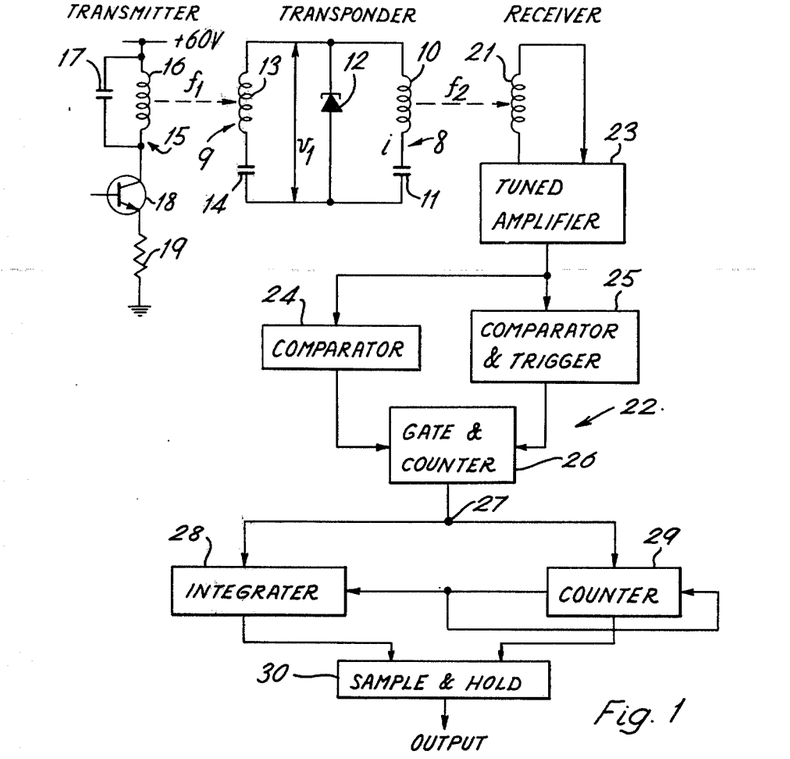
FIG. 1 is a part-circuit part-block diagram including up-converter apparatus according to the invention.

In FIG. 1 a coil 10 and a capacitor 11 form a series resonant circuit 8 coupled across a tunnel diode 12. Either the coil 10 or the capacitor 11 may be, or may include, a transducer whose reactance varies in accordance with a quantity measured. A further resonant circuit 9 connected across the tunnel diode 12 comprises a coil 13 and a capacitor 14. The two resonant circuits 8 and 9 have different resonant frequencies $f_1$ and $f_2$, respectively.

Signals are induced in the coil 13 by transmissions from a transmitter 15 having a parallel resonant circuit resonant at the frequency $f_1$ and comprising a coil 16 and a capacitor 17. The resonant circuit of the transmitter 15 is shown driven by a transistor 18 having an emitter resistor 19 connected in series with the coil 16 across a 60 volt supply.

Figure 2:
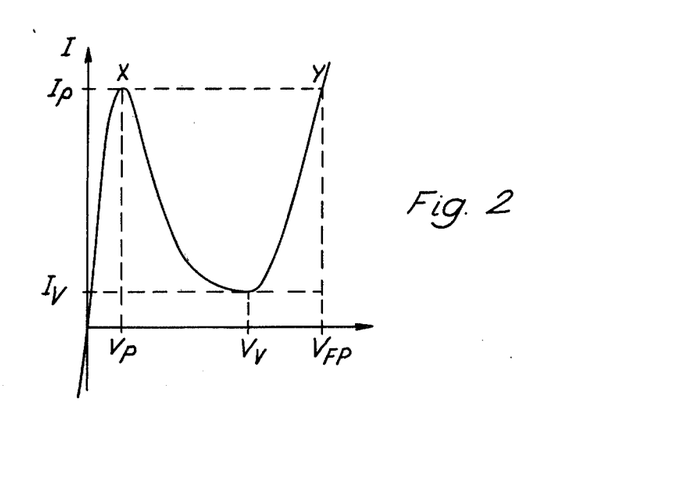
FIG. 2 is a typical static characteristic for a tunnel diode.
Figure 3A:
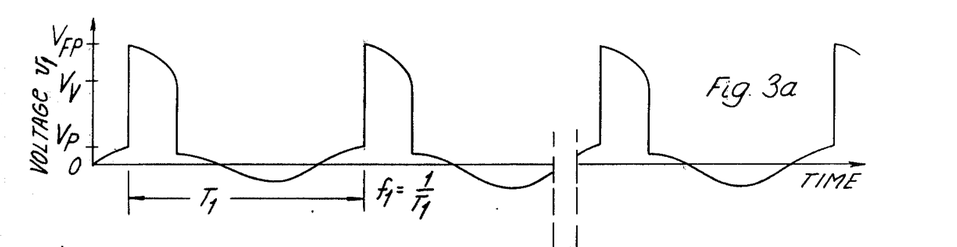
FIGS. 3(a) to 3(g) are waveforms occurring in the circuit of FIG. 1.

The tunnel diode 12 acts as a negative resistance switching element and is voltage driven by an e.m.f. $v_1$ across the resonant circuit 9. When the tunnel diode is driven into its negative resistance region ($v_1 < V_p$- see FIG. 2) the diode changes from a high current, low voltage state $X(I_p, V_p)$ in FIG. 2 to a high current, high voltage state $Y(I_p, V_{fp})$. As the induced e.m.f. in the coil 13 decreases the voltage across the diode decreases to $V_v$ and then makes a fast transition to near zero volts. When the induced e.m.f. becomes positive again, point X is reached on the characteristic, and the switching cycle is repeated. The resultant voltage waveform across the diode 12 is shown in FIG. 3(a) and comprises a series of fast rise-time pulses at a repetition frequency $f_1$, the magnitude of each pulse being much larger than the induced voltage in the coil 13.

The tunnel diode acts as a voltage pulse generator driving the resonant circuit 8 and the low series impedance of the diode enables a high quality factor (Q) to be maintained and helps to provide isolation between the circuits 8 and 9. The circuit 8 rings at its resonant frequency with the waveform shown in FIG. 3(b), damped oscillation being caused by both edges of the driving waveform of FIG. 3(a).

In choosing the various frequencies and components for the circuit of FIG. 1, the choice must be such that the coil 13 and the capacitor 14 present a high impedance at the frequency $f_2$; and the coil 10 and the capacitor 11 present a high impedance at the frequency $f_1$. Clearly $f_2$ must be greater than $f_1$ (hence the transponder is an up-converter) and both frequencies must be sufficiently high to restrict the size of the coils and capacitors used.

In one example of the circuit of FIG. 1, $f_1 = 200$ kHz and $f_2 = 10$ MHz. The coils 10, 13 and 16 in this example have inductances of 1.5 $\mu$H, 60 $\mu$H and 2.4 $\mu$H, respectively, while a coil 21 in a receiver unit has an inductance of 1 $\mu$H. Capacitors 11, 14 and 17 have capacities of 160 pF, 10,000 pF and 0.25 $\mu$F respectively. The tunnel diode used is type IN 3718 (General Electric). The series resistance of the coil 10 has a value of 1 ohm and that of the coil 13 is 3 ohms.

The coil 10 is coupled by electro-magnetic induction to the coil 21 of a receiver 22 whose purpose is to provide an output voltage proportional to the frequency $f_2$. Signals from the coil 21 pass to an amplifier 23 tuned to cover the frequency range in which the frequency $f_2$ falls. From the amplifier 23 signals pass to a comparator 24 which produces rectangular pulses of equal height at a repetition frequency $f_2$. A further comparator 25 also coupled to the output of the amplifier 23 provides trigger pulses (shown in FIG. 3(d)) having a leading edge coincident with the beginning of each burst of pulses from the comparator 24 and having a trailing edge timed to occur between bursts of such pulses. Each trigger pulse enables a gate and counter circuit 26 to provide signal pulses each lasting while five pulses from the comparator 24 are counted.

Figure 3B:
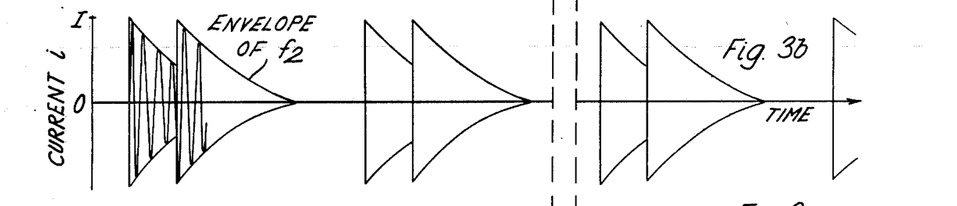
Figures 3C, 3D, 3E:
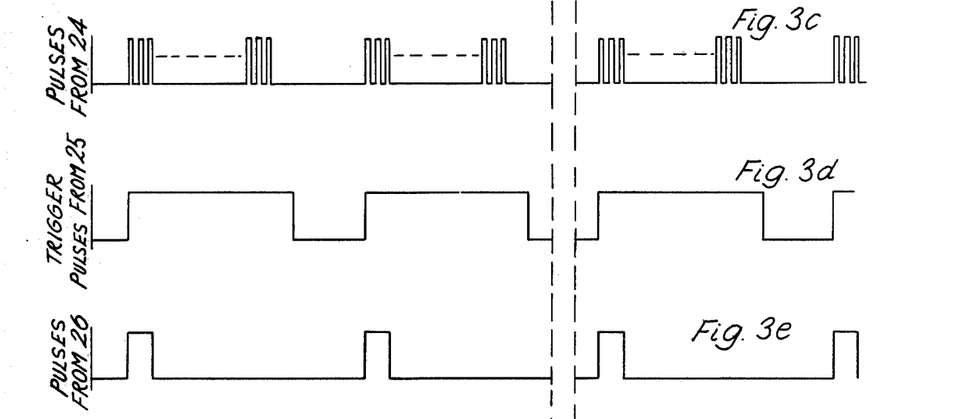
Figure 3F:
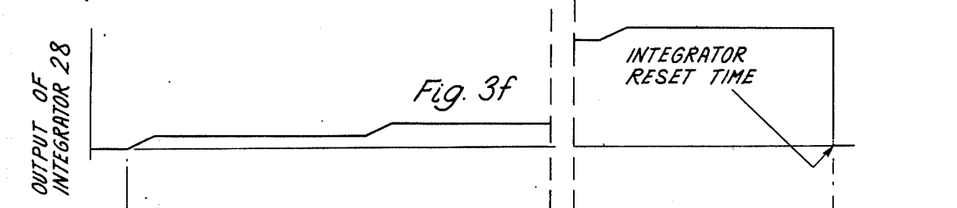
Figure 3G:
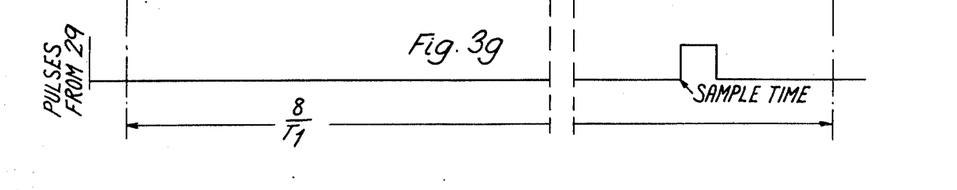

Thus the waveform of FIG. 3(e) is obtained at the point 27 and this waveform comprises a series of pulses each having a duration proportional to $5/f_2$ seconds. The pulses are supplied to an integrator 28 whose output waveform is shown in FIG. 3(f) and the integrator is reset by a counter 29 after eight pulses from the circuit 26 have been counted. At the same time a sample and hold circuit 30 is gated at the time shown in FIG. 3(g) and the integrator output held until a new sample is taken. Each sample output is a voltage proportional to 40 cycles of $f_2$ providing an indication of this frequency and hence of the quantity measured by the transducer formed by the coil 10 or the capacitor 11.

With the components and frequencies mentioned the system operates to a distance of 20 cms. between both transmitter and transponder, and transponder and receiver. Where an inductance displacement transducer was used as part of the coil 10, a change of twenty-five microns caused an output voltage level from the sample and hold circuit 30 of fifty millivolts. As an example of a dental application, a transponder of approximate dimensions 25 mm. by 10 mm. and containing a small inductance pressure gauge has been attached to a dental plate to allow pressure measurement in the buccal cavity.

The transducer may, for example where pressure is to be measured, comprise an E-shaped ferrite core with a few turns of copper wire wound round the central arm of the 'E'. The core is contained in a porcelain housing with the limbs of the E pointing vertically upwards. The top of the housing is formed by an acrylic diaphragm and a ferrite disk is fixed under the diaphragm opposite the limbs of the E. The ferrite disc can move so varying the reluctance path of the ferrite core and altering the inductance at the terminals of the coil.

In a typical transducer of this type a 5 lb. force/square inch increase in pressure causes the receiver output voltage to change by about 60 mV corresponding to a change in $f_2$ of about 1.25%.

Three orthogonal transmitter and/or receiver coils may be used to reduce signal drop out. Using the arrangement shown in FIG. 1 the orientation of the transponder may be changed by up to 90°. The coils 10, 13, 16 and 21 may be in the same plane or the coils 10 and 21 in one plane with the coils 13 and 16 is an orthogonal plane. The problem of signal variations due to relative movements, particularly in orientation, between parts of the system can be at least partially overcome by switching between orthogonal aerials as described by Jacob, R., Riddle H., and Watson, B.W.: "Circuit for searching for a signal from a three aerial system during inductive loop telemetry", Biomedical Engineering, Vol. 8, No. 7, 1973, pp. 292–295. (This equipment is manufactured by Rigel Research Ltd., Sutton, Surrey, England).

Figure 9:
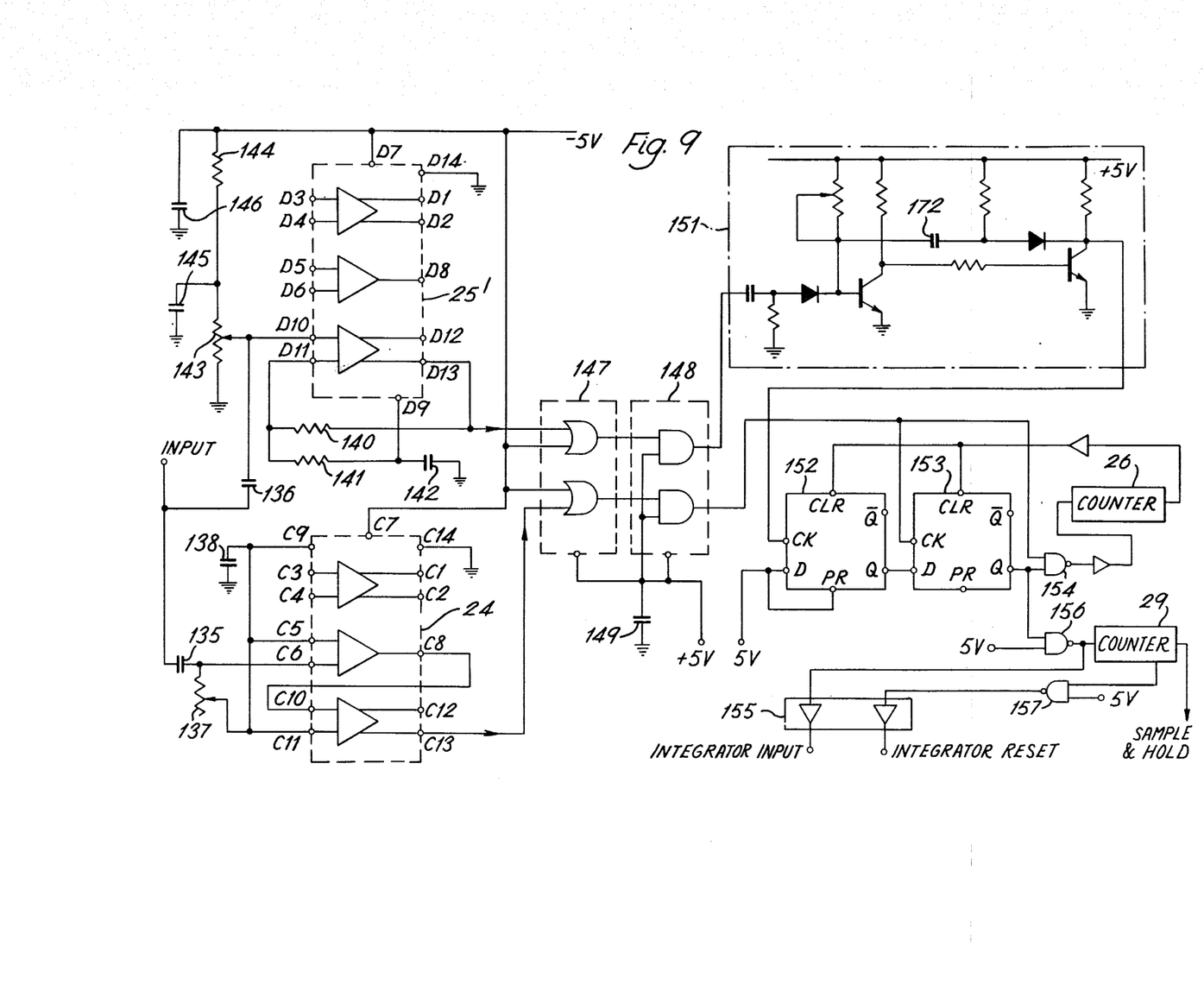
FIG. 9 is a circuit diagram of part of the circuit of FIG 1.

Some of the circuits of FIG. 1 will now be discussed in more detail with reference to FIG. 9 where the comparator 24 and a comparator portion 25' of the circuit 25 are each shown as Motorola integrated circuits type MC 1035 (emitter coupled logic). The signal from the tuned amplifier 23 reaches the comparators 24 and 25' by way of one microfarad capacitors 135 and 136. In the comparator 24 two sections of the integrated circuit are connected in series and used as differential amplifiers. One input of each amplifier is coupled to ground by way of a 0.1 microfarad capacitor 138 so that two zero-crossing detector circuits in series are formed and the output waveform of FIG. 3c appears at an output terminal C13. (In this specification where a designation is preceded by a letter that designation corresponds to the maker's terminal number).

Only one differential amplifier section of the circuit 25' is used and this section is given a "hysteresis" characteristic by means of the components connected between terminals D9, D11 and D13: a 100 ohm resistor 140, a 47 ohm resistor 141, and a 0.1 microfarad capacitor 142 connected to earth, the output being taken from the terminal D13.

The hysteresis characteristic requires a voltage of about 0.1 volts at a terminal D10 before an output signal appears at the terminal D13 but the input voltage has to be reduced to about −0.1 volts before the output signal is removed. This characteristic ensures that only the first few cycles of each burst of ringing as shown in FIG. 3b cause corresponding output pulses at the terminal D13.

Further components required for the comparators 24 and 25' include 5 K ohm potentiometers 137 and 143, a 680 ohm resistor 144, a 0.1 microfarad capacitor 145 and a 1 microfarad capacitor 146.

The outputs from the integrated circuits 24 and 25' are converted to TTL logic levels by Motorola integrated circuit 147-type MC 1068 and buffered by an integrated circuit type 148-type SN 7400, Texas Instruments, which requires a 1 microfarad capacitor 149.

The output from the comparator 25' is passed to a monostable trigger circuit 151 where the leading edge of the first pulse causes the circuit to enter its unstable state. A timing capacitor 172 and its associated resistors causes a return to the stable state after an interval longer than each burst of ringing but shorter than the repetition period of bursts with the result that the waveform of FIG. 3d appears at the monostable output.

This waveform is required to trigger the counting of pulses from the comparator 24 and is passed to a bistable circuit 152. When the bistable circuit is set it prepares a further bistable circuit 153 for setting and this occurs when the next pulse from the comparator 24 reaches the clock terminal of the circuit 153. The Q output of the bistable circuit 153 then provides an input for an NAND gate 154 and when this gate is open the pulses from the comparator 24 reach the counter 26 which is an integrated circuit SN 7490 (Texas Instruments). After the counter 26 has counted five pulses from the comparator 24 it clears the bistable circuits 152 and 153 so closing the gate 154.

The output waveform of the bistable circuit 153 is thus as shown in FIG. 3e and is ready for application by way of a NAND gate 156 to the counter 29 which is formed by a Texas Instruments integrated circuit SN 74162 and to the integrator itself by way of an inverter forming part of a Texas Instruments integrated circuit 155 type SN 7405. When the counter 29 has reached the count eight it sends a "sample and hold" signal to the circuit 30 and resets the integrator by way of a NAND gate 157 and another inverter in the circuit 155. The NAND gates 156 and 157 provide input signals of suitable polarity and are in the form of Texas Instruments type SN 7410 integrated circuits.

Figure 4:
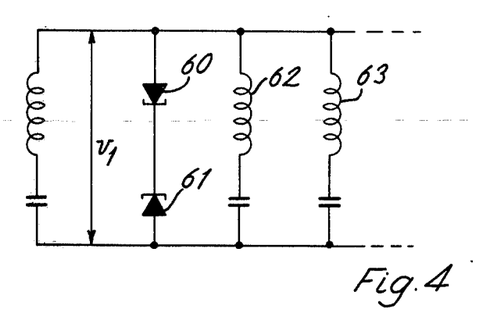
FIG. 4 is a circuit diagram of another apparatus according to the invention.
Figure 5:
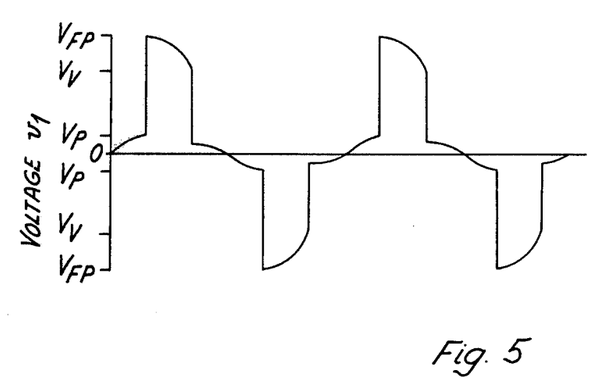
FIG. 5 is a waveform occurring in the circuit of FIG. 4.

FIGS. 4 and 5 illustrate the use of two tunnel diodes 60 and 61 back to back, and multichannel operation. In other arrangements a single tunnel diode and multichannel operation, or the two diodes and single channel operation can be used. Multichannel telemetry may be achieved by using more than one transmit resonant circuit in parallel across the tunnel diode (or diodes). Two such resonant circuits 62 and 63 are shown in FIG. 4, each having a variable resonant frequency restricted to a frequency band such that the bands due to the different circuits do not overlap. The receiver then includes multiplex decoding circuits for identifying the different frequencies, using time division multiplex or parallel receiver circuits. Using the two tunnel diodes back to back doubles the rate of generation of pulse edges driving the transmit resonant circuit or circuits as can be seen from FIG. 5 where both positive and negative pulses are shown, and thus the data rate is doubled. In the reverse voltage direction a tunnel diode acts as a low impedance (see FIG. 2).

Figure 6:
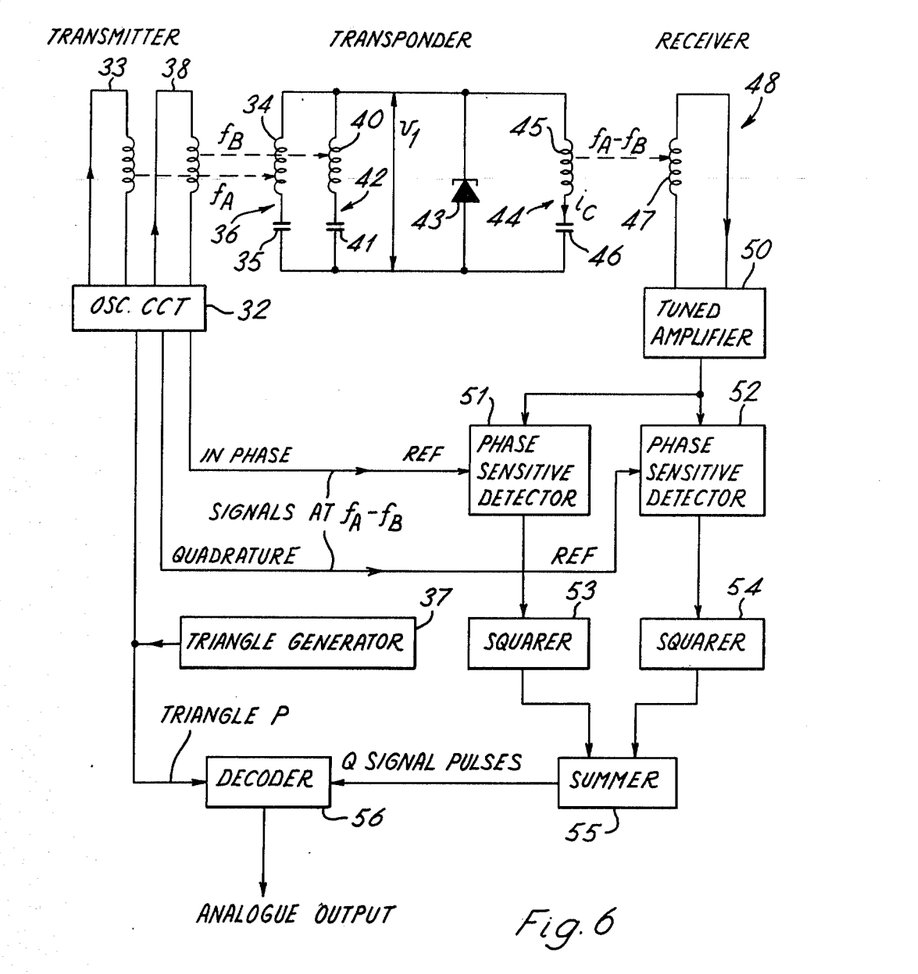
FIG. 6 is a part-circuit part-block diagram including down-converter apparatus according to the invention, FIGS. 7(a) and (b) and 8(a) and (b) are waveforms occurring in the circuit of FIG. 6.

In the circuit of FIG. 6 an oscillator circuit 32 has two outputs: a signal at a fixed frequency $f_A$ feeding a coil 33; and a signal at a frequency $f_B$ which is swept by ±50 kHz feeding a coil 38. The sweep is controlled by a triangular waveform generator 37 having the waveform shown in FIG. 8(b). The generator 37 may be an integrated-circuit function generator (Signetics type NE 566) as discussed on pages 62 to 63 of the booklet by the Signetics Corporation (1972) entitled "Phase locked loops applications book", and that part of the oscillator circuit providing the swept frequency may be constructed in one of the two ways described on pages 55 to 56 and 64 to 65, respectively, of the same booklet. The coil 33 transmits to a coil 34 in series with a capacitor 35 which together form a resonant circuit 36 resonant at the frequency $f_A$. The coil 38 transmits to a transponder coil 40 in series with a capacitor 41 together forming a resonant circuit 42 resonant at the frequency $f_B$. Both resonant circuits 36 and 42 are situated in a transponder.

Figure 7A:
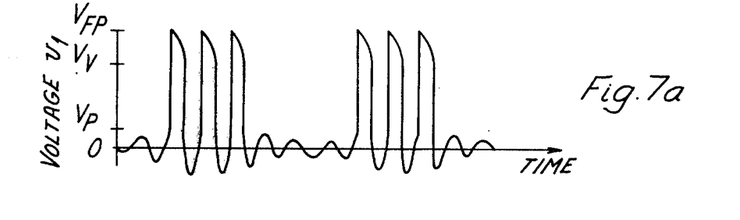
Figure 7B:
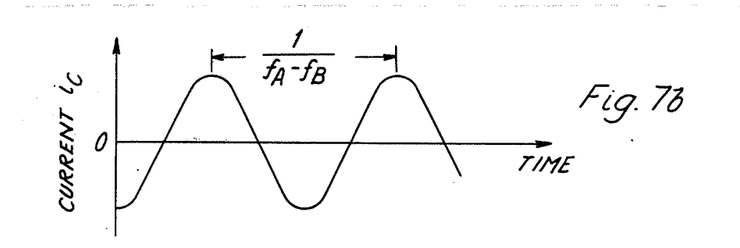

A tunnel diode 43 is connected across the two resonant circuits 36 and 42 and is switched in bursts of pulses which appear at the difference frequency $f_A-f_B$ (see FIG. 7(a)). A circulating current shown in FIG. 7(b) now flows through a resonant circuit 44 which includes a coil 45 and a capacitor 46 together resonant at a frequency in the range swept by $f_A-f_B$ as $f_B$ varies. This resonant frequency is determined by the current condition of a transfer forming the whole or part of one of the components of the circuit 44.

A coil 47 in a receiver 48 picks up the signal from the coil 45 and applies it to an amplifier 50 tuned to cover the range in which the signal $f_A-f_B$ falls.

Now as the signal at the frequency $f_B$ is swept it varies cyclically raising to a maximum frequency and then falling to a minimum frequency and so on. In sweeping in this way the signals in the resonant circuit 44 rise sharply to a maximum value as the resonant frequency of the circuit is swept through in approaching the maximum frequency and then again rise to another peak as this frequency is again swept through when the signal $f_B$ falls to a minimum. Hence the output from the amplifier 50 comprises a series of pulses evenly spaced in time on either side of the time at which $f_B$ reaches a minimum.

Since the frequency $f_A-f_B$ is known at any given time from the outputs of the oscillator circuit 32, this information can be used to decode the pulses at the output of the amplifier 50 with maximum signal to noise ratio. This process is carried out by using two phase sensitive detectors 51 and 52 fed with in-phase and quadrature reference signal at the frequency $f_A-f_B$, respectively. The phase sensitive detectors in integrated circuits Signetics type NE 562 (phase locked loops) may be used for the circuits 51 and 52. By squaring the output from the phase sensitive detectors in squaring circuits 53 and 54 and summing the result in a summing circuit 55, a modulus output is obtained whatever phase relationship exists between the output from the amplifier 50 and the reference signals. Thus the circuits 51 to 55 have, in effect, a very high Q and filter out any unwanted signals in the output from the amplifier 50.

The squarers 53 and 54 may be based on the circuit described on pages 51 and 52 of the "Applications manual for operational amplifiers", published by Philbrick/Nexus Research, (second edition 1968). A typical summing circuit is given on page 41 of the above mentioned Philbrick/Nexus applications manual.

Figure 8A:
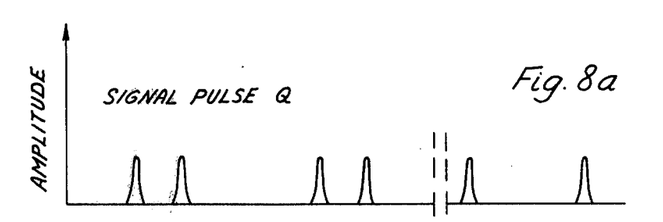
Figure 8B:
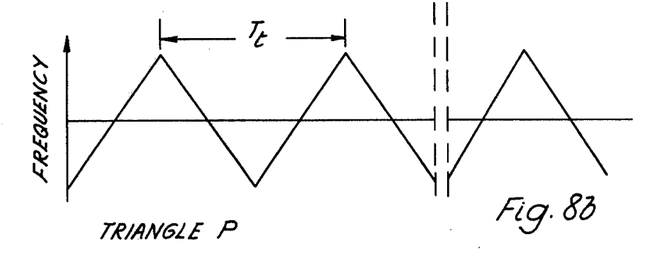

The waveform of the signal from the summing circuit 55 is shown in FIG. 8(a). Both this waveform and the triangular waveform from the generator 37 are applied to a decoder circuit 56 which converts the intervals between the groups of pulses in FIG. 8(a) to a voltage level. It will be seen that this interval varies as the resonant frequency of the circuit 44 varies, since for a comparatively low resonant frequency the interval between the times this frequency is swept as $f_B$ rises and then falls will be comparatively small. The interval depends on the transducer impedance and thence on the quantity measured.

Typical values for $f_A$ and $f_B$ are $f_A=5.1$ MHz and $f_B=5.0$ MHz (swept±50 kHz).

In the decoder circuit 56 a Schmitt trigger circuit (not shown) converts the narrow signal pulses Q to voltage levels suitable to drive a bistable circuit (not shown) also part of the decoder. The output of this bistable circuit is a series of pulses of fixed amplitude whose width is proportional to the intervals between groups of the pulses Q. A smoothing circuit (not shown) in the decoder circuit smooths the fixed amplitude pulses to provide the analogue output of the decoder. The bistable circuit in the decoder is set to the correct initial state on switch on by circuits (not shown), also part of the decoder, for monitoring the amplitude and slope of the triangular waveform.

Although the invention has been specifically described in connection with FIGS. 1, 4 and 6 it will be clear that it can be put into practice in many other ways. For example another form of transducer which may be used is the varactor diode which can take the place of a capacitor in a resonant circuit and allows voltage measurements to be carried out and transmitted to the receiver. Any of the resonant circuits may include a piezoelectric crystal acting as an ultrasonic transmitter and in some cases additionally as a transducer. Where transmission to or from the transducer is by ultrasonics, ultrasonic receivers must, of course, be used as appropriate. For example low frequency piezo-electric ultrasonic transducers (Vernitron 20.5 kHz Airmaster and Vernitron 40 kHz Sonair transducers), with power ratings of about 0.25 W have been used in the link between the transmitter and transponder. Piezo-electric transducers have a relatively high impedance ($\simeq$1 K ohm) so that impedance matching using transformer coupling between such a transducer and the transponder non-linearity is generally required.

In relation to FIG. 6 the subtraction of the signals at the frequencies $f_A$ and $f_B$ may be carried out before transmission so that only a single transmitter coil is required instead of the coils 33 and 38 and only a single receiver resonant circuit centred on the frequency $f_A + f_B$ is required in the transponder to replace the resonant circuits 36 and 42.

Further the circuits 51 to 55 may be replaced by a vector voltmeter. The co-ordinate method detects the in-phase and quadrature components of the signal, whereas the vector voltmeter method uses feedback to ensure that the signal and reference voltages are always in phase. This means that the output of a phase sensitive detector (P.S.D.) 160 (see FIG. 10) is always a maximum, since the mean output of a P.S.D. is proportional to $\cos \theta$ where $\theta$ is the phase angle between the input signal and the reference signal. A reference signal from the transmitter at frequency $f_A - f_B$ is passed to a phase shift circuit 162 which imparts a phase shift equal to the phase error between the reference and the received signal, the phase shift being controlled as described below. A P.S.D. 163 which also receives the reference signal from the phase shift circuit 162 will have a finite mean output until the reference signal is in quadrature to the incoming signal when the output will be zero, and hence the phase error is also zero. The reference signal will then be in phase with the received signal and thus the output of the P.S.D. 160 will be a maximum. Feedback by way of a low-pass filter 164 ensures that the output of the P.S.D. 163 is always zero and therefore the output of the P.S.D. 160 is always a maximum. Another low-pass filter 165 smooths the vector voltmeter output before it is passed to the decoder 56 of FIG. 6.

Figure 10:
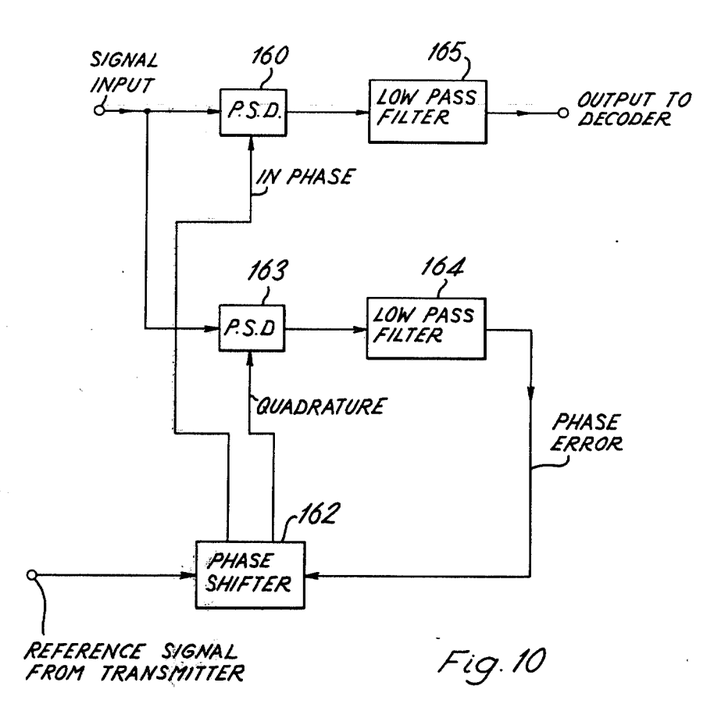
FIG. 10 is a block diagram of a circuit which may be used as an alternative to part of the circuit of FIG. 6.

In this telemetry application the input signal to the vector voltmeter is in the form of a pulse. However, due to the use of feedback the vector voltmeter needs a finite time to lock on to the incoming signal, the required time being a function of the characteristic of the low pass filter 164. Since a pulse is being detected the response time of the system must be fast and this means that the low-pass filter 164 must have a large bandwidth. Increasing the low-pass filter bandwith increases the bandwidth of the whole system making it more susceptible to noise pick-up and also increases the ripple at the output. The output of the vector voltmeter is a pulse, which occurs every time the swept input frequency corresponds to the resonant frequency of the secondary tuned circuit of the transponder and hence the output signal is decoded in circuit 56 to determine the instantaneous frequency of the received signal.

Figure 11:
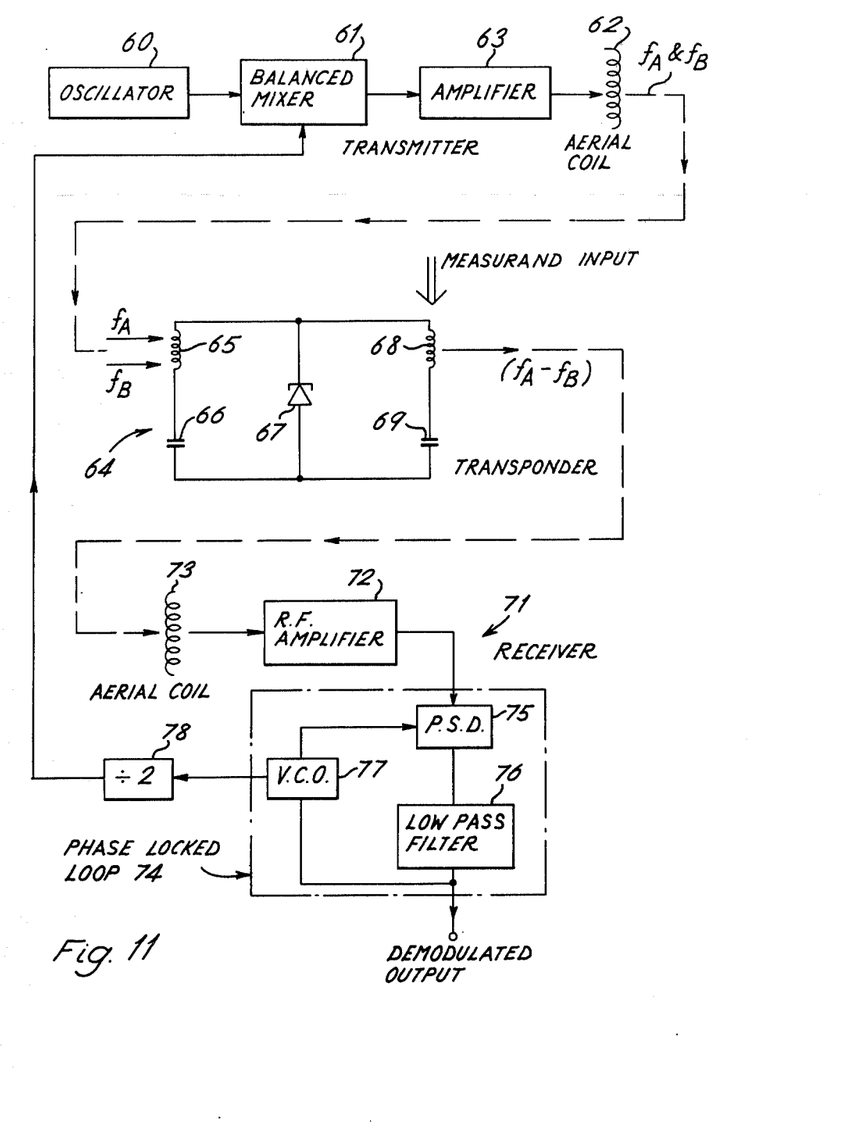
FIG. 11 is a part-circuit part-block diagram including further down-converter apparatus according to the invention.

A further embodiment of a down-converter system is shown in FIG. 11 where phase locked loop detection is employed with the advantage that the signal from the transponder is continuous.

A 28 MHz sinewave oscillator 60 provides a carrier signal for a balanced mixer 61. A modulating signal for the mixer, nominally at 0.5 MHz, is provided by the receiver in a way which will be explained later. The sum and difference frequencies from the mixer 61 are applied to an aerial coil 62 by way of an amplifier 63 and the two signals transmitted $f_A$ and $f_B$ have the nominal frequencies 28.5 MHz and 27.5 MHz respectively.

A transponder 64 has a first series-resonant circuit comprising an inductor 65 and a capacitor 66 which is resonant at 28 MHz. As in previous embodiments this resonant circuit is connected across a tunnel diode 67 and in parallel with a second resonant circuit comprising an inductor 68, which includes a transducer and a capacitor 69. The amplitude of the combined signal comprising the frequencies $f_A$ and $f_B$ is such that the tunnel diode switches in groups of pulses at the difference frequency $f_A - f_B = 1$ MHz in the same way as is shown in FIG. 7a. The second resonant circuit is resonant at 1 MHz and thus the current flowing in this resonant circuit is a continuous sinewave similar to that shown in FIG. 7b. The voltage waveform across the inductor 68 is a sinusoid of amplitude about 1 volt peak to peak and this signal is transmitted to and detected by a receiver 71.

An RF amplifier 72 coupled to an aerial coil 73 feeds a phase locked loop 74 which includes a phase-sensitive detector 75, a low-pass filter 76 and a voltage-controlled oscillator 77. The loop attempts to keep a reference signal from the voltage controlled oscillator 77 (nominally at 1 MHz) in phase quadrature with the signal from the transponder 64 since when this relationship occurs the output signal from the low-pass filter 76 which smooths the output of the phase-sensitive detector 75 is at a minimum. When a change occurs in the inductor 68, the phase relationship between the signal received from the transponder and the reference signal from the voltage controlled oscillator also changes. As a result the frequency of the signal from the voltage-controlled oscillator and thus the output signal of a divide-by-two circuit 78 is varied, changing the frequency of the modulating signals for the balanced mixer 61 (nominally at 0.5 MHz) in a sense which alters the difference frequency $f_A - f_B$ to the new resonant frequency of the second resonant circuit. In this way the frequency of the voltage-controlled oscillator locks on to the resonant frequency of the second resonant circuit; and the output signal from the low-pass filter 76 is indicative of this frequency and is directly related to the quantity to be measured. In a fully operational system constructed according to FIGS. 11 and 12 the relationship between the output of the low-pass filter and the pressure applied to the transducer is linear. The second resonant circuit is thus always supplied with a difference frequency which allows it to resonate and so a continuous signal is sent to the receiver 71.

The receiver 71 can be basically similar to a normal FM radio receiver and may have a narrow bandwidth improving the receiver output signal-to-noise ratio.

Some of the circuits shown in FIG. 11 will now be discussed in more detail. Firstly the balanced mixer 61 is based on a double-balanced mixer integrated circuit type SN 76514 (Texan Instruments). The amplifier 63 is a tuned amplifier having a bandwidth of about 2 MHz centres on 28 MHz and the aerial coil 62 is tuned by a capacitor (not shown).

In the transponder 64 the inductor 65 has an inductance of 0.7 microhenrys and the capacitor 66 has a capacitance of 50 pF. A type 1N 3718 tunnel diode may be used and the capacitor 69 has a value of 2200 pF. The inductor 68 is made up of a three microhenry aerial coil in series with a variable inductance transducer having a nominal value of 8 microhenrys.

The transducer may be as already described in connection with the circuit of FIG. 1 except that a 50 micro-meters movement of the diaphragm causes a change in the inductance at the terminals of the coil of between about 8 and 11 microhenrys. Typically, the sensitivity of the transducer is about 0.2 volts/lb force/square inch for pressures up to 5 lb force/square inch.

In the receiver 71, the amplifier 72 comprises three stages: a tuned cascode amplifier based on the MC 1550 (Motorola) integrated circuit, a common emitter stage and an emitter follower stage. Automatic gain control is provided. The voltage gain is about 77 dB at 1 MHz with a bandwidth of about 0.25 MHz centreed on 1 MHz.

Figure 12:
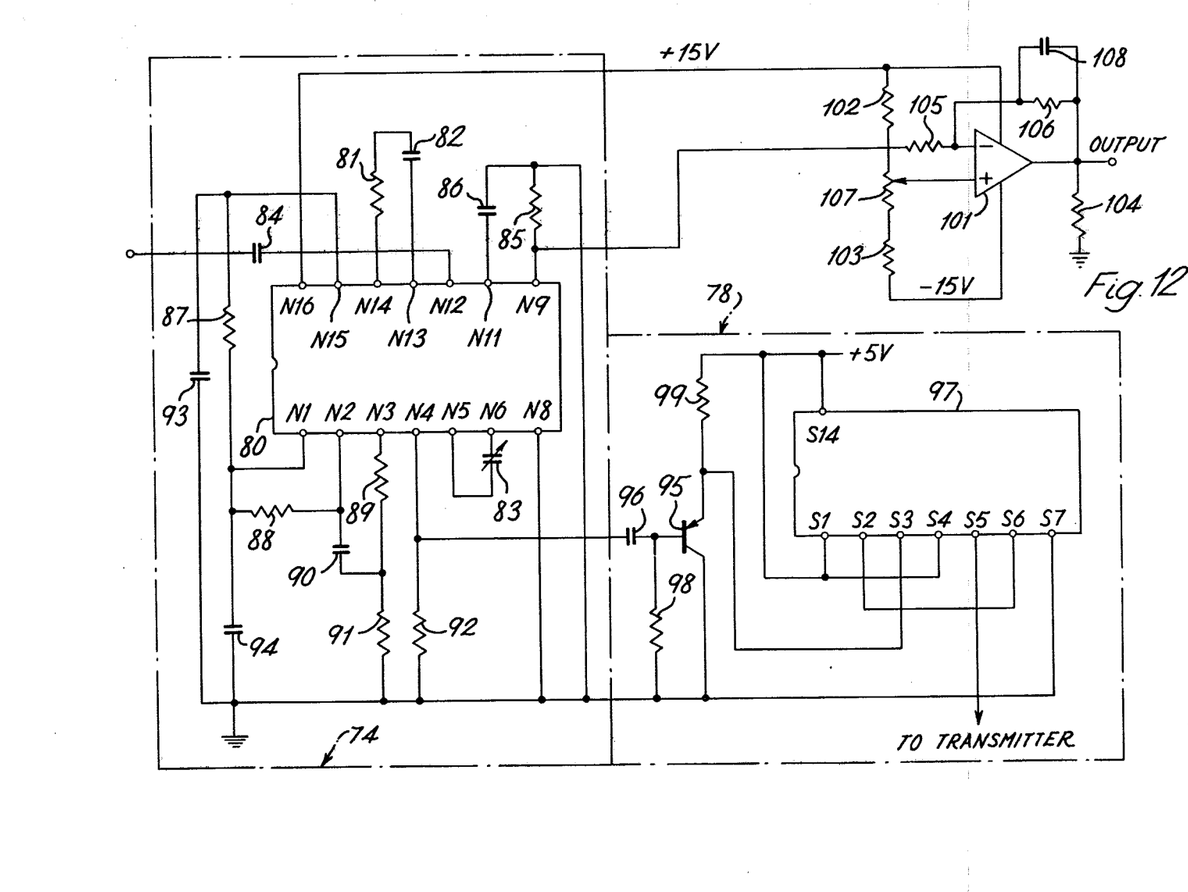
FIG. 12 is a circuit diagram of part of the circuit of FIG. 11.

The phase locked loop detector is shown in more detail in FIG. 12. The main section is formed by a Signetics integrated circuit 80 (phase locked loop) type NE 562, the bandwidth of which is set to 1 kHz by means of the low-pass filter 76 formed by a 100 ohm resistor 81 and a 0.47 microfarad capacitor 82 connected in series with one another between terminals N14 and N13 of the integrated circuit 80. The free-running frequency of the voltage control oscillator 77 is adjusted to 1 MHz by a variable capacitor 83 of nominal value 300 pF connected between terminals N5 and N6. The input from the amplifier 72 passes by way of a 0.1 microfarad capacitor 84 to a terminal N12 and the demodulated output appears at a terminal N9. To bias and decouple the integrated circuit 80 various other components whose values are determined according to the usual methods are required. These components are listed below with exemplary values:

Resistor 85: 15 K ohm
Resistors 87, 88 and 89: 1 K ohm
Resistor 91: 11 K ohm
Resistor 92: 12 K ohm
Capacitors 86, 90, 93 and 94: 0.1 microfarads A type BC 213 transistor 95 coupled to a terminal N4 of the integrated circuit 80 by way of a 0.01 microfarad capacitor 96 passes the nominally 1 MHz signal from the oscillator 77 to a D type bistable circuit 97 (Texas Instruments type SN 7474) and adjusts the output of the oscillator to TTL logic levels. The transistor 95 has a base bias resistor 98 of 10 K ohms and a load resistor 99 of 47 K ohms. The emitter of the transistor is coupled to a terminal S3 of the bistable circuit 97 which forms the frequency divider 78. The output at 0.5 MHz from the flip-flop 97 is obtained at a terminal S5 and supplied to the balanced mixer 61.

The demodulated output from the phased locked loop at a terminal N9 of the integrated circuit 80 is amplified by an operational amplifier 101 (type SN 72741, Texas Instruments) to provide a d.c. telemetry output. The bandwidth of the operational amplifier is limited to 200 Hz to attenuate unwanted noise further. Various components for operating the amplifier 101 are listed as below but are chosen according to conventional techniques:

Resistors 102 and 103: 10 K ohms
Resistor 104: 15 K ohms
Resistor 105: 100 K ohms
Resistor 106: 1 Megohm
Variable resistor 107: Nominally 20 K ohms
Capacitor 108: 2200 pF Many possible modifications for the circuit of FIG. 11 are, of course, possible, for example a rejection filter may be added at the input of the receiver 71 to reject transmitter frequencies around 28 MHz, and the transmitter formed by the components 60 to 62 may be modified to provide a pulsed waveform in which each burst of pulses is followed by a gap between bursts. The mark space ratio of the duration of each burst to the duration of the gaps may then advantageously be unity. A waveform of this type may be used with an ultrasonic link between the transmitter and the transponder. Of course operation at different frequencies than those specifically mentioned is possible, for example at lower frequencies the carrier frequency could be 5 MHz with a difference frequency of 100 kHz.

Figure 13:
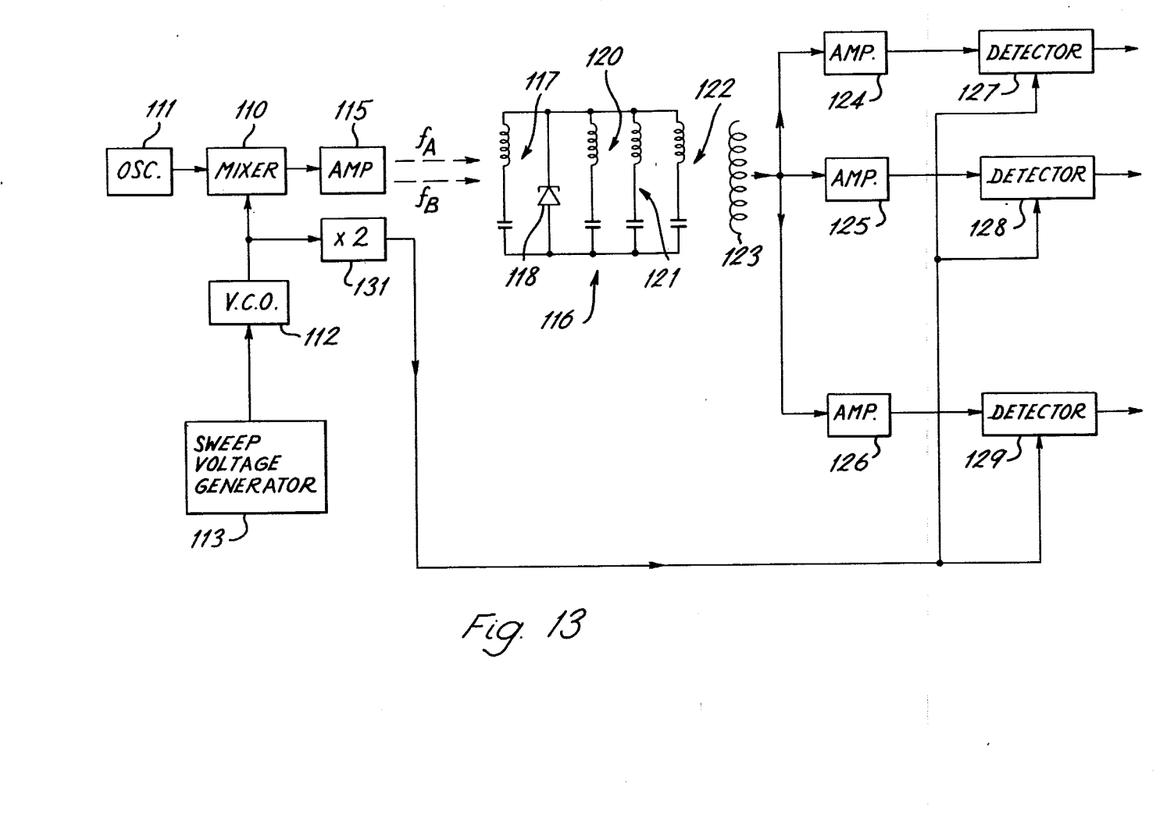
FIG. 13 is a block diagram including a multiplex down-converter according to the invention.

An example of a multiplex down-converter system is shown in FIG. 13. A balanced mixer 110 receives a high frequency signal at 10 MHz from oscillator 111 and a low frequency signal swept between about 40 kHz and 225 kHz from a voltage controlled oscillator 112 controlled by a sweep voltage generator 113.

After passing through amplifier 115 the output from the mixer is transmitted to a transponder 116 having a receive resonant circuit 117 tuned to 10 MHz and with a pass-band of about 0.5 MHz in order to pass the full swept range of the difference frequency. As before the transponder includes a tunnel diode 118 but now has three resonant circuits 120, 121 and 122 tuned to different frequencies connected in parallel across it. In this example the circuits 120, 121 and 122 are tuned to 100 kHz, 200 kHz and 400 kHz, respectively. The inductances in these circuits include, of course, transducers and the maximum variation in the resonant frequency is about ±5%. Thus the circuits have resonant frequency variations of 95 to 105 kHz; 190 to 210 kHz and 380 to 420 kHz, respectively. The difference frequency must therefore be swept from 95 to 420 kHz and in practice this means that the sweep must be from about 80 kHz to 450 kHz. Hence the sweep already quoted for the voltage controlled oscillator 112.

In the receiver a receive aerial 123 is connected to three amplifiers 124, 125 and 126 one in each of three channels. The amplifiers 124, 125 and 126 are of a relatively high Q value and are tuned to 100 kHz, 200 kHz and 400 kHz, respectively, their output signals being passed to detector circuits 127, 128 and 129. Each of these circuits may be of the type shown in FIG. 6 or a vector voltmeter of the type shown in FIG. 10. To this end and assuming a vector voltmeter, a reference signal is supplied from the voltage controlled oscillator 112 by way of a multiply-by-two circuit 131 and three telemetry output signals are available from the three detector circuits 127 to 129.

We claim:

1. Information-transmission apparatus comprising:
   a transmitter for transmitting signals at a first frequency, and transponder apparatus including:
   a non-linear device having a non-linear impedance,
   a receive resonant circuit connected to the non-linear device for obtaining power from transmissions from the transmitter to vary the non-linear impedance of the said device and generate a non-sinusoidal waveform across the device when transmissions are received, the receive resonant circuit being at least broadly tuned to a frequency range in which the first frequency occurs,
   a transmit resonant circuit, resonant at a second frequency, connected to the non-linear device, and
   transducer means for varying the resonant frequency of the transmit resonant circuit;
   a receiver having a receiving circuit at least broadly tuned to a frequency range in which the second frequency occurs; and
   a frequency indicating circuit, coupled to the receiving circuit, for providing a signal indicative of the frequency of a signal received by the receiving circuit.

2. Apparatus according to claim 1 wherein the receive resonant circuit is resonant at the first frequency, the transmit resonant circuit includes a transducer the impedance of which varies in accordance with a value which is, to be transmitted, of a quantity, the variation of the transducer impedance, in operation, varying the resonant frequency of the second resonant circuit.

3. Apparatus according to claim 1 wherein the non-linear device is a step-recovery diode.

4. Apparatus according to claim 1, wherein:
   the non-linear device is a negative resistance device, having a pair of terminals between which positive and negative resistances appear when the voltage applied between the terminals varies; and
   the receive resonant circuit is connected to the said terminals to vary the voltage applied to the said terminals, and cause, when signals of at least a predetermined strength are induced therein, the resistance of the device to vary cyclically between positive and negative resistance.

5. Apparatus according to claim 1, wherein:
   the transmitter includes means for transmitting signals at a sweep frequency, in addition to the first frequency, the sweep frequency varying cyclically over a predetermined frequency range;
   the receive resonant circuit of the transponder is resonant at the first frequency;
   the transponder includes a further receive resonant circuit resonant at substantially the center of the swept frequency range, the further receive resonant circuit being connected, in addition to the other receive resonant circuit, to the non-linear device to vary the non-linear impedance thereof;
   the transmit resonant circuit is constructed to position the second frequency within the range of difference frequencies arising between the first and sweep frequencies; and
   the receiving circuit of the receiver is tuned to cover the said range of difference frequencies.

6. Apparatus according to claim 5, wherein the transmit resonant circuit includes a transducer, the impedance of which varies in accordance with a value, which is to be transmitted, of a quantity, the variation of the transducer impedance, in operation, varying the resonant frequency of the second resonant circuit.

7. Apparatus according to claim 5, wherein the non-linear device is a tunnel diode.

8. Apparatus according to claim 5, wherein:
   the non-linear device is a negative resistance device, having a pair of terminals between which positive and negative resistances appear when the voltage applied between the terminals varies; and
   the receive resonant circuits are connected to the said terminals to vary the voltage applied to the said terminals, and cause, when signals of at least a predetermined strength are induced therein, the resistance of the device to vary cyclically between positive and negative resistance, the cyclic variation between positive and negative resistance occurring in intervals which are also cyclic and occur with a repetition frequency equal to the instantaneous difference frequency between the first frequency and the sweep frequency.

9. Apparatus according to claim 1, wherein:
   the transmitter includes means for transmitting the signal at the first frequency simultaneously with another signal at a third frequency, the difference between the first and third frequencies being small compared with each of the first and second frequencies;
   the transmitter also includes control means for varying the difference between the first and third frequencies in response to a control signal;
   the receive resonant circuit of the transponder is tuned to cover the range defined by the first and third frequencies;
   the transmit resonant circuit is constructed to position the second frequency within the range of possible difference frequencies arising between the first and third frequencies as limited by the maximum possible variations in the said control signal;
   the receiving circuit is broadly tuned to the said range of difference frequencies; and
   the frequency-indicating circuit of the receiver, in operation, generates the control signal at a value which, in operation, maintains the difference frequency arising between the first and third frequencies equal to the second frequency.

10. Apparatus according to claim 9, wherein:
    the transmit resonant circuit includes a transducer, the impedance of which varies in accordance with a value, which is to be transmitted, of a quantity, the variation of the transducer impedance, in operation, varying the resonant frequency of the second resonant circuit; and
    the frequency indicating circuit is constructed to maintain the control signal at a value which maintains the difference frequency substantially equal to the second frequency as the second frequency varies with changes in the impedance of the transducer.

11. Apparatus according to claim 9, wherein the non-linear device is a tunnel diode.

12. Apparatus according to claim 9, wherein:
    the non-linear device is a negative resistance device, having a pair of terminals between which positive and negative resistances successively appear when the voltage applied between the terminals varies; and
    the receive resonant circuit is connected to the said terminals to vary the voltage applied to the said terminals, and cause, when signals of at least a predetermined strength are induced therein, the resistance of the device to vary cyclically between positive and negative resistance, the cyclic variation between positive and negative resistance occurring in intervals which are also cyclic and occur with a repetition frequency equal to the difference frequency between the first and third frequencies.

13. Apparatus according to claim 1, including: a number of further transmit resonant circuits connected to the non-linear device, each transmit resonant circuit having a resonant frequency which varies over a range unique to that circuit.

14. Apparatus according to claim 4 wherein the transmit and receive resonant circuits are connected in parallel with one another across the said terminals of the negative resistance device.

15. Apparatus according to claim 4 wherein the negative resistance device includes two tunnel diodes connected in series with one another but oppositely poled with respect to one another.

16. Apparatus according to claim 4 including a number of further transmit resonant circuits each including a transducer, the receive and the transmit resonant circuits being connected in parallel with one another across the said terminals of the negative resistance device, and each transmit resonant circuit having a range of resonant frequency variation which is unique to that circuit.

17. Apparatus according to claim 5 wherein the frequency-indicating circuit includes first and second phase-sensitive detectors coupled to receive the output of the receiving circuit and first and second reference signals, respectively, at the instantaneous difference frequency between the first and sweep frequencies, the first reference signals being in phase quadrature with the second reference signal, means for squaring the outputs of the phase-sensitive detectors, means for summing the resultant signals, and means for providing an output signal indicative of the interval between cyclic first and second output pulses from the summing means which each occur once during each frequency cycle of the sweep frequency.

18. Apparatus according to claim 5 wherein the frequency-indicating circuit includes a vector-voltmeter circuit and means for providing an output signal indicative of the interval between cyclic first and second output pulses from the vector-voltmeter circuit which each occur once during each frequency cycle of the sweep frequency.

19. Apparatus according to claim 9, wherein the transmitter includes an oscillator, the control means includes a balanced-mixer circuit coupled to receive the output signal of the oscillator as one of two input signals, and the frequency-indicating circuit includes a phase-locked loop circuit providing a variable frequency signal, varying in accordance with the said second signal, and means for supplying the control signal as the other input signal for the balanced mixer in accordance with the said variable frequency signal.

20. Apparatus according to claim 19 wherein the phase-locked loop circuit includes a phase-sensitive detector coupled to receive the output signal from the receiving circuit, a voltage-controlled oscillator for supplying a reference signal to the phase-sensitive detector, and a low-pass filter coupled at the output of the phase-sensitive detector to provide the output signal indicative of the said difference frequency and to provide a voltage to control the voltage controlled oscillator, and wherein the means for supplying the said other input signal includes a divide-by-two circuit for dividing the frequency of the output signal of the voltage controlled oscillator by two and passing the resultant signal as the control signal to the balanced mixer.

21. Apparatus according to claim 1 wherein transmission between the transmitter and the transponder apparatus, or between the transponder apparatus and the receiver is by electron-magnetic induction, or microwave transmission.

22. Apparatus according to claim 1 wherein transmission between the transmitter and the transponder apparatus, or between the transponder apparatus and the receiver is by microwave transmission.

23. Apparatus according to claim 1 wherein transmission between the transmitter and the transponder apparatus, or between the transponder apparatus and the receiver is by ultrasonic transmission.

24. Apparatus according to claim 2 wherein the transducer includes a piezo-electric crystal.

25. Transponder apparatus including:
a non-linear device having a non-linear impedance;
a receive resonant circuit, connected to the non-linear device, for obtaining power from transmissions by a transmitter to vary the non-linear impedance of the said device and generate a non-sinusoidal waveform across the device when transmissions are received, the receive resonant circuit being at least broadly tuned to a first frequency;
a transmit resonant circuit, resonant at a second frequency, connected to the non-linear device to apply the non-sinusoidal waveform to the transmit resonant circuit to cause oscillations to occur therein; and
transducer means for varying the resonant frequency of the transmit resonant circuit.

26. Apparatus according to claim 5, wherein the transmit and receive resonant circuits are connected in parallel with one another across the non-linear device.

27. Apparatus according to claim 9, wherein the transmit and receive resonant circuits are connected in parallel with one another across the non-linear device.

28. An apparatus as in claim 1, wherein said receive resonant circuit has a resonant frequency $f_1$ and said transmit resonant circuit has a resonant frequency $f_2$, said receive resonant circuit presenting a high impedance of frequency $f_2$ and said transmit impedance presenting a high impedance at frequency $f_1$, frequency $f_2$ being greater than $f_1$.

29. An apparatus as in claim 1, wherein said non-linear device is a step recovery diode.

30. An apparatus as in claim 1, wherein said non-linear device is a semiconductor junction diode.

31. Apparatus according to claim 1 wherein transmission between the transmitter and the transponder apparatus, or between the transponder apparatus and the receiver is by optical transmission.

32. Apparatus according to claim 1, wherein transmission between the transmitter and the transponder apparatus employs a different mode of transmission from transmission between the transponder apparatus and the receiver.

33. Information-transmission apparatus comprising:
A. a transmitter for transmitting signals at a first frequency, and transponder apparatus including:
a non-linear device having a non-linear impedance,
a receive resonant circuit connected to the non-linear device for obtaining power from transmissions from the transmitter to vary the non-linear impedance of the said device and generate a non-sinusodial waveform having a plurality of harmonic frequencies across the device when transmissions are received, the receive resonant circuit being at least broadly tuned to a frequency range in which the first frequency occurs, a transmit resonant circuit, resonant at a second frequency, connected to the non-linear device for oscillation in response to a harmonic of said non-sinusoidal waveform having the resonant frequency of said transmit resonant circuit, and transducer means for varying the resonant frequency of the transmit resonant circuit;

B. a receiver having a receiving circuit at least broadly tuned to a frequency range in which the second frequency occurs; and C. a frequency indicating circuit, coupled to the receiving circuit, for providing a signal indicative of the frequency of a signal received by the receiving circuit.

* * * * *